US010835319B2

(12) United States Patent
Falardeau et al.

(10) Patent No.: US 10,835,319 B2
(45) Date of Patent: Nov. 17, 2020

(54) COMPUTER-ASSISTED SURGERY SYSTEM AND METHOD FOR CALCULATING A DISTANCE WITH INERTIAL SENSORS

(71) Applicant: ORTHOSOFT, INC., Montreal (CA)

(72) Inventors: Bruno Falardeau, Verdun (CA); Catherine Proulx, Verdun (CA); Herbert Andre Jansen, Freiburg (DE); Benoit Pelletier, Laval (CA); Jonathan Tardif, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 244 days.

(21) Appl. No.: 15/720,531

(22) Filed: Sep. 29, 2017

(65) Prior Publication Data

US 2018/0085171 A1    Mar. 29, 2018

Related U.S. Application Data

(60) Provisional application No. 62/401,424, filed on Sep. 29, 2016.

(51) Int. Cl.
*A61B 34/20* (2016.01)
*A61B 34/10* (2016.01)
(Continued)

(52) U.S. Cl.
CPC .............. *A61B 34/10* (2016.02); *A61B 34/20* (2016.02); *A61B 34/25* (2016.02); *A61B 34/70* (2016.02);
(Continued)

(58) Field of Classification Search
CPC ......... A61B 34/10; A61B 34/20; A61B 34/25; A61B 34/70; A61B 2034/2048;
(Continued)

(56) References Cited

U.S. PATENT DOCUMENTS 9,167,989 B2 * 10/2015 Odermatt ................. A61B 5/06
2009/0247863 A1   10/2009 Proulx
(Continued)

FOREIGN PATENT DOCUMENTS

| EP | 2 542 177 A1 | 1/2013 |
| EP | 2 957 249 A1 | 12/2015 |
| WO | 2012012863 A1 | 2/2012 |

*Primary Examiner* — Jessica Weiss
(74) *Attorney, Agent, or Firm* — Norton Rose Fulbright Canada LLP

(57) ABSTRACT

A computer-assisted surgery system for obtaining a distance between at least two fixed points relative to a bone comprises a first accelerometer unit located at a first fixed location on the bone, and producing first acceleration data during a movement of the bone. A second accelerometer unit is located at a second fixed location on the bone, and simultaneously producing second acceleration data during the movement. A gyroscope unit is fixed to the bone and simultaneously producing angular rates of change of said movement. A processor unit obtains the acceleration data and the angular rates of change for calculating the distance between the first fixed position and the second fixed position on the bone using a distance value of a distance vector between the accelerometer units. An interface outputs the distance between the first fixed position and the second fixed position relative to the bone. A method for calculating a distance between at least two points on a bone is provided.

10 Claims, 3 Drawing Sheets

(51) Int. Cl.
*A61B 34/00* (2016.01)
*A61B 90/00* (2016.01)

(52) U.S. Cl.
CPC .............. *A61B 2034/2048* (2016.02); *A61B 2034/2055* (2016.02); *A61B 2090/061* (2016.02); *A61B 2090/3983* (2016.02); *A61B 2090/3991* (2016.02)

(58) Field of Classification Search
CPC ...... A61B 2034/2055; A61B 2090/061; A61B 2090/3983; A61B 2090/3991
USPC ........................................................ 606/102
See application file for complete search history.

(56) References Cited

U.S. PATENT DOCUMENTS

| | | | |
|---|---|---|---|
| 2012/0277634 A1 | 11/2012 | Proulx | |
| 2013/0172906 A1* | 7/2013 | Olson | A61B 34/71 606/130 |
| 2016/0007909 A1* | 1/2016 | Singh | A61F 2/4657 606/102 |
| 2019/0201155 A1* | 7/2019 | Gupta | A61B 5/06 |

* cited by examiner

COMPUTER-ASSISTED SURGERY SYSTEM AND METHOD FOR CALCULATING A DISTANCE WITH INERTIAL SENSORS

CROSS-REFERENCE TO RELATED APPLICATIONS

The present application claims the priority of U.S. patent application Ser. No. 62/401,424, filed on Sep. 29, 2016 and incorporated herein by reference.

TECHNICAL FIELD

The present disclosure relates to a method and system using inertial sensors in computer-assisted surgery.

BACKGROUND OF THE ART

Computer-assisted surgery has been developed in order to help the operator in performing alterations to a bone. Among the various tracking technologies used in computer-assisted surgery, optical navigation, C-arm validation and manual reference guides have been used. The optical navigation requires the use of a navigation system, which adds operative time. It is also bound to line-of-sight constraints that hamper the normal surgical flow. C-arm validation requires the use of bulky equipment and the validation is not cost-effective. Moreover, it is generally used post-operatively as opposed to intra-operatively. Accordingly, inertial sensors are used for their cost-effectiveness and the valuable information they provide. Since inertial sensors have no need for an external reference, they may be immune to environmental factors such as magnetic fields and operate under a wide range of conditions. However, inertial sensor units are primarily used to provide orientation data, as opposed to positional data.

SUMMARY

In accordance with a first embodiment of the present disclosure, there is provided a method for calculating a distance between at least two points on a bone, comprising: obtaining, using one or more processors within a computing system, first acceleration data from a first accelerometer unit located at a first fixed location relative to the bone, during a movement of the bone; simultaneously obtaining, using the one or more processors within the computing system, second acceleration data from at least a second accelerometer unit at a second fixed location relative to the bone, during said movement; simultaneously obtaining, using the one or more processors within the computing system, angular rates of change from at least one gyroscope unit fixed to the bone, during said movement; and calculating and outputting, using the one or more processors within the computing system, a distance value of a distance vector between the first fixed position and the second fixed position using the angular rates of change of the at least one gyroscope unit and the acceleration data of the accelerometer units.

In accordance with a second embodiment of the present disclosure, there is provided a computer-assisted surgery system for obtaining a distance between at least two fixed points relative to a bone, comprising: a first accelerometer unit located at a first fixed location on the bone, and producing first acceleration data during a movement of the bone; at least a second accelerometer unit located at a second fixed location on the bone, and simultaneously producing second acceleration data during said movement; at least one gyroscope unit fixed to the bone and simultaneously producing angular rates of change of said movement; a processor unit obtaining the acceleration data and the angular rates of change for calculating the distance between the first fixed position and the second fixed position on the bone using a distance value of a distance vector between the accelerometer units; and an interface to output the distance between the first fixed position and the second fixed position relative to the bone.

In accordance with a third embodiment of the present disclosure, there is provided a system for obtaining a distance between at least two fixed points relative to a bone, the system comprising: a processor unit; and a non-transitory computer-readable memory communicatively coupled to the processing unit and comprising computer-readable program instructions executable by the processing unit for: obtaining first acceleration data from a first accelerometer unit located at a first fixed location relative to the bone, during a movement of the bone; simultaneously obtaining second acceleration data from at least a second accelerometer unit at a second fixed location relative to the bone, during said movement; simultaneously obtaining angular rates of change from at least one gyroscope unit fixed to the bone, during said movement; calculating and outputting a distance value of a distance vector between the first fixed position and the second fixed position using the angular rates of change of the at least one gyroscope unit and the acceleration data of the accelerometer units.

DETAILED DESCRIPTION

Figure 1:
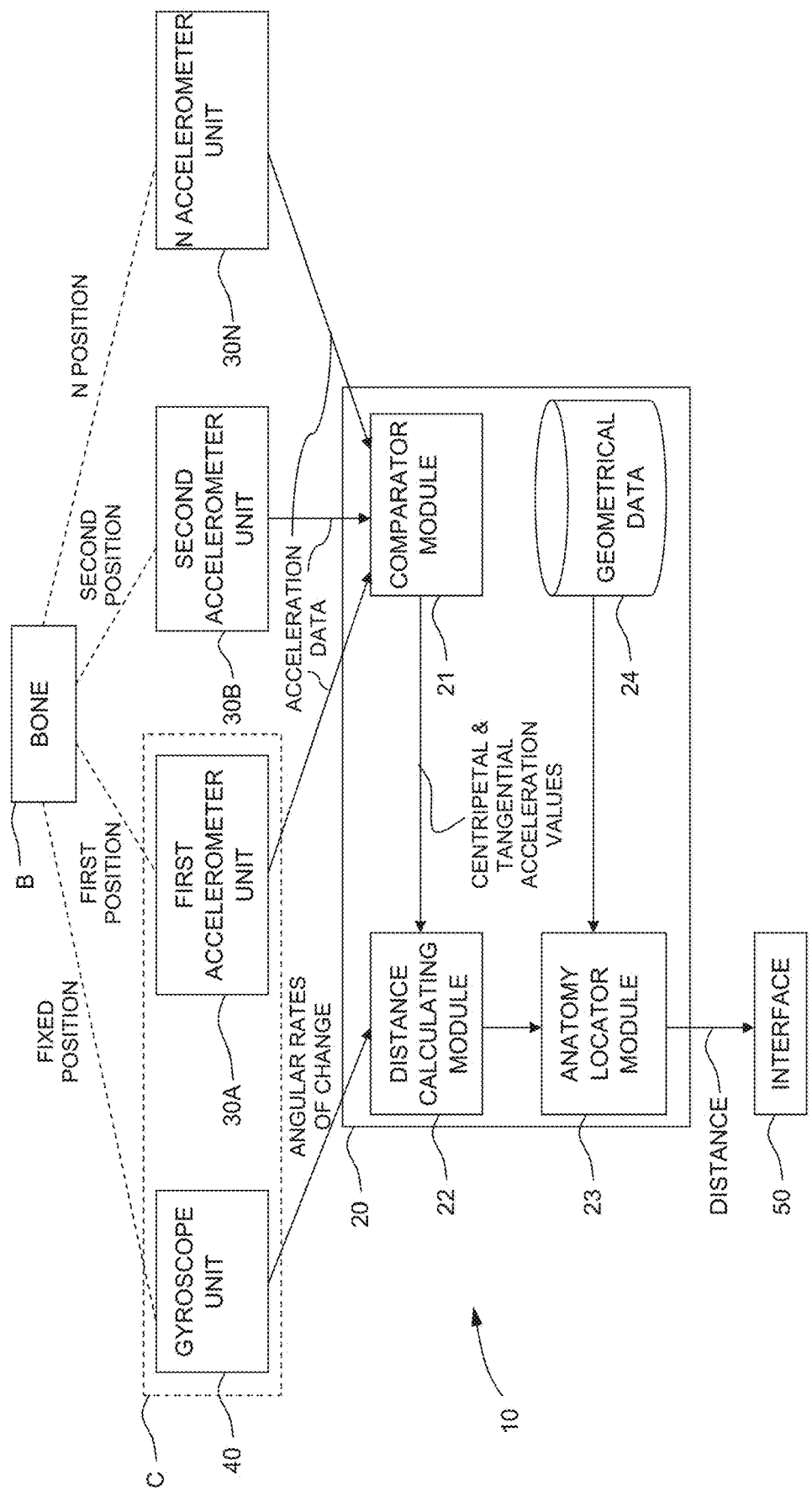
FIG. 1 is a block diagram of a computer-assisted surgery system for calculating a relative position between at least two points relative to a bone.

Referring to the drawings and more particularly to FIG. 1, a computer-assisted surgery system for obtaining a distance between points on a bone is generally illustrated at 10. The system 10 comprises a computer-assisted surgery (CAS) processor unit 20 receiving data from accelerometer units 30A, 30B and 30n and a gyroscope unit 40, commonly referred to as the sensors or inertial sensors. The system 10 outputs data by way of a user interface(s) 50, in the form of a screen, a monitor, a portable device, LEDs, indicator lights, a data file, etc.

Figure 2:
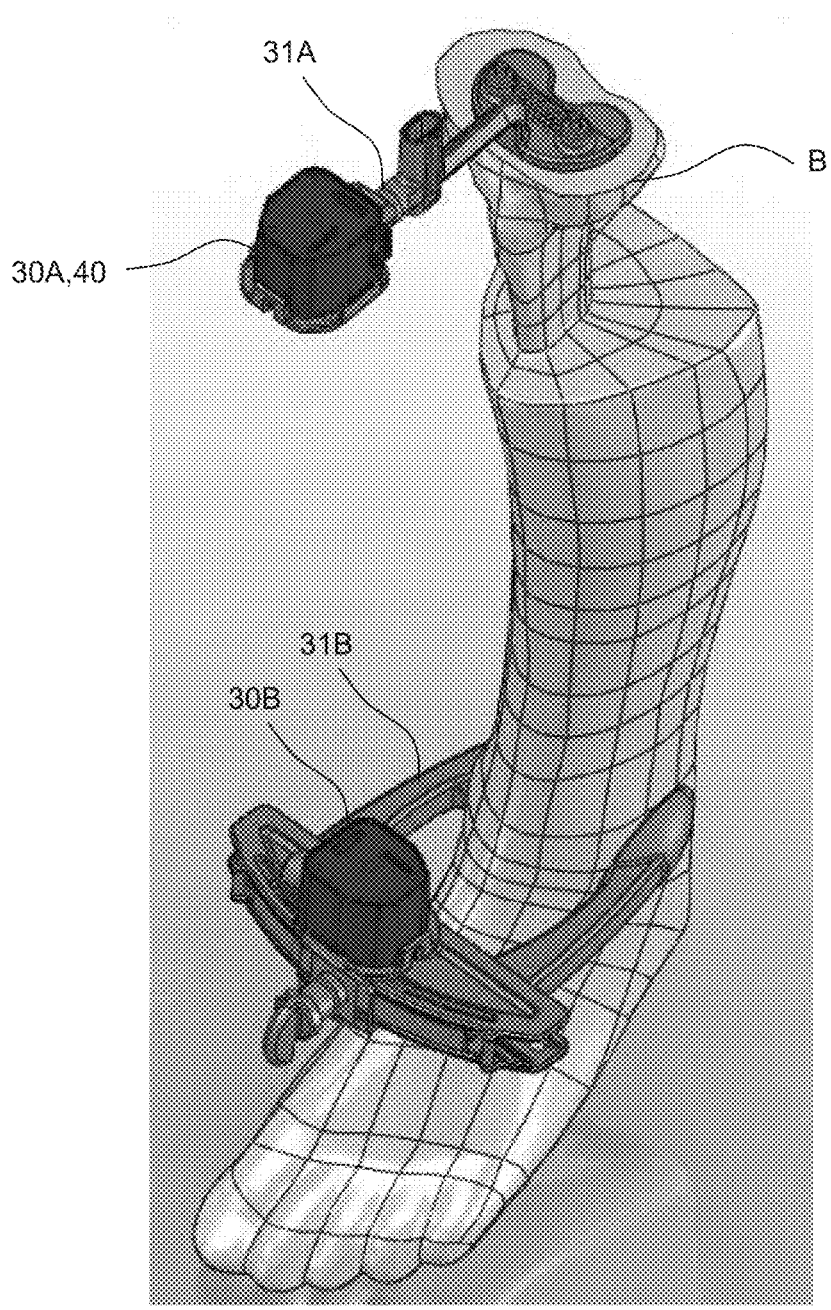
FIG. 2 is an exemplary schematic view of a position of accelerometers on the bone.

As observed in FIG. 2, the first accelerometer unit 30A is located at a first fixed location on the bone B, and produces first acceleration data for movements of the bone B. The expression "fixed" is used to indicate that the various sensors are in an immovable position and orientation on the bone B, whether it be by straps, bone anchoring, mechanical clamps, etc. The use of the expression "fixed" used throughout incorporates the various possible manners to attach the sensors to the bone.

The second accelerometer unit 30B is located at a second fixed location on the bone B, and simultaneously produces second acceleration data during the movements of the bone B. The gyroscope unit 40 is also fixed to the bone B and simultaneously produces angular rates of change for the movements of the bone B. As shown the first accelerometer unit 30A and the gyroscope unit 40 may be packaged into a single sensor device C, for practicality, i.e., in a common casing. However, the gyroscope may be secured at its own location on the bone B, provided it is in a fixed relation on the bone B. Although not shown, n additional accelerometer units 30n may be fixed at other locations on the bone B. As the system 10 measures distances between the accelerometer units 30 (i.e., 30A, 30B, 30n), more distance values may be obtained by having more accelerometer units.

In the exemplary set-up of FIG. 2, the system 10 may be used to validate a tibial cut in the context of a total knee arthroscopy. This is one of the possible applications for the system 10, and is provided as an example. Other applications are for leg length discrepancy measurement for hip joint surgery (by comparison with a pre-operative leg length (i.e., native, pre-resection, etc)), and humerus length measurement in shoulder surgery, for example. The sensor device C is placed on the tibial cut, the tibial cut being the first fixed location on the bone B. The sensor device C may have a support bracket 31A with a spike aligned with the mechanical axis entry point so that the position of the sensor device 10 relative to a mechanical axis of the bone B is known. The support bracket 31A may have a plate portion 32A that has an underface lying flat against the tibial cut. In some procedures, holes are drilled in the tibial cut to eventually receive pegs of an implant. The plate 32A may have projections positioned thereon as a function of the holes previously drilled. This may be as a result of pre-operative planning. An arm 33A may extend forwardly from the plate 32A and have a receptacle for releasably receiving (e.g., quick coupling) the sensor device C, for example in a known geometric relation. In an embodiment, the sensor device C is coupled to the support bracket 31A by a connection system as described in U.S. patent application Ser. No. 13/724,060, filed on Dec. 21, 2012, the contents of which are incorporated herein by reference.

The accelerometer unit 30B is attached to the malleoli, with a self-centering mechanism 31B, so that the accelerometer unit 30B is aligned with the ankle center. This is one possible arrangement. The self-centering mechanism 31B is for instance described in U.S. Pat. No. 8,551,108, incorporated herein by reference. Other types of supports may be used. This includes for example brackets pinned or attached/connected to the bone in any appropriate way provided the accelerometer units 30 are fixed, and even connecting the sensor device C directly to the bone. The present method and system are not limited to specific support brackets.

The CAS processor unit 20 is of the type having processing means with the computing capacity for the equations described below, and including a non-transitory computer-readable memory communicatively coupled to the processing unit 20 and comprising computer-readable program instructions, for instance in the form of modules, executable by the processing unit 20 for performing steps as described below. The CAS processor unit 20 may be a stand-alone computer connected to the various sensors, by wired or wireless communication, with the various sensors having the wired or wireless communication capability as well. It is however pointed out that the CAS processor unit 20 may be partially or integrally integrated into one of the sensor units (a.k.a., pod) used, such as the sensor device C integrating both the first accelerometer unit 30A and the gyroscope unit 40. The sensor device C, when incorporating the CAS processor unit 20, may thus be equipped with user interfaces 50 to provide the navigation data, whether it be in the form of LED displays, screens, numerical displays, etc. However, as the computer-assisted knee surgery system described herein may use more than one of the inertial sensor units, it is considered to have a stand-alone CAS processor unit to receive data from all inertial sensors and give the operator centralized guidance. This may also include local guidance by having data indicators on the inertial sensors, such as indicator lights or displays for given parameters (flexion/extension, varus/valgus, anteversion, inclination, cut length, etc, depending on the nature of the application).

The processor unit 20 receives the acceleration data from the accelerometer units 30 fixed to the single rigid body, i.e., the bone B in FIG. 2, and the angular rates of change from the gyroscope unit 40 and is used to output a distance between the fixed points of the bone B, among other possible values. The processor unit 20 may calculate the relative position (i.e., the distance) between the accelerometers 30, i.e., between the fixed positions of the accelerometers 30A and 30B of FIG. 2, in the following manner.

At any moment t, during unconstrained movements of the bone including a rotational component of movement other than about an axis passing through a pair of the accelerometer units (i.e., multiple motions about multiple non parallel axes), the acceleration data perceived by the accelerometer units 30 can be divided into four components: a translation component, a rotation component (i.e. the centripetal acceleration), a tangential component and a gravity component.

$$\vec{a}_{total} = \vec{a}_{gravity} + \vec{a}_{translation} + \vec{a}_{centripetal} + \vec{a}_{tangential}$$

At the same moment t, the gyroscope output, i.e., the angular rates of change, can be decomposed into an instantaneous rotation axis $\vec{A} = (A_x, A_y, A_z)$ and a rotational velocity magnitude w. As the accelerometer units 30 and the gyroscope unit 40 are all rigidly fixed to the same body, e.g., the bone B, the accelerometer units 30 and the gyroscope unit 40 generally perceive the same rotational velocity.

For the accelerometer units 30, the translation and gravity components in the bone coordinate system are the same. Therefore, the processor unit 20 has a comparator module 21 for isolating a centripetal acceleration value and a tangential acceleration value for each of the accelerometer units 30 by comparing the first acceleration data with the second acceleration data, as the difference between the acceleration data output by the accelerometer units is only due to the rotational and tangential components, namely:

$$\vec{a}_{total_2} - \vec{a}_{total_1} = (\vec{a}_{centripetal_2} + \vec{a}_{tangential_2}) - (\vec{a}_{centripetal_1} + \vec{a}_{tangential_1})$$

A distance calculating module 22 of the processor unit 20 may use the centripetal acceleration value and the tangential acceleration value of each said accelerometer unit 30, along with the angular rates of change of the gyroscope unit 40, to calculate a distance between each accelerometer unit 30. By definition, the centripetal acceleration is:

$$|\vec{a}_{centripetal_i}| = \omega^2 r_i$$

Also by definition of the centripetal acceleration, the centripetal acceleration is towards the center of rotation. Let $\vec{v}_i$ be $\vec{a}_{centripetal_i}$ normalized.

$$\vec{v}_i = \frac{\vec{a}_{centripetal_i}}{\omega^2 r_i}$$

Let $\vec{d}_{12} = (d_x, d_y, d_z)$ be the vector between the positions of two accelerometer units 30. If both centripetal acceleration vectors are projected in the plane normal to the instantaneous rotation axis, the following is obtained:

$$\vec{d}_{12_{proj}} = r_1\vec{v}_1 - r_2\vec{v}_2$$

$$= \frac{\vec{a}_{centripetal_1} - \vec{a}_{centripetal_2}}{\omega^2}$$

$$= \frac{1}{\omega^2}((\vec{a}_{total_1} - \vec{a}_{tangential_1}) - (\vec{a}_{total_2} - \vec{a}_{tangential_2}))$$

$$= \frac{1}{\omega^2}(\Delta\vec{a}_{tangential} - \Delta\vec{a}_{total})$$

where $$\Delta\vec{a}_{tangential} = \vec{a}_{tangential_2} - \vec{a}_{tangential_1}$$

and $$\Delta\vec{a}_{total} = \vec{a}_{total_2} - \vec{a}_{total_1}$$

The $\vec{a}_{total}$ term of each accelerometer unit 30 is fully known, while the tangential acceleration has to be evaluated from the known data. By the definition of tangential acceleration, $$|\vec{a}_{tangential_i}| = r_{t_i}\frac{\Delta\omega}{\Delta t}$$

where $r_{t_i}$ is the tangential acceleration radius. This value can be different from the previously defined radius (towards the center of rotation), but since the tangential instant center is the same for the two accelerometer units 30, the difference between the two tangential radiuses remains $\vec{d}_{12}$.

To know the tangential acceleration of a point in space, this equation may be extended to the vector form and perform the cross product of these two values.

$$\vec{a}_{tangential_i} = r_{t_i}\vec{v}_i \times \frac{\Delta\vec{\omega}}{\Delta t}$$

The $\Delta\vec{a}_{tangential}$ term may be computed from the previous equation, $$\Delta\vec{a}_{tangential} = r_{t_2}\vec{v}_2 \times \frac{\Delta\vec{\omega}}{\Delta t} - r_{t_1}\vec{v}_1 \times \frac{\Delta\vec{\omega}}{\Delta t} = \vec{d}_{12} \times \frac{\Delta\vec{\omega}}{\Delta t}$$

By extending the cross product calculation, the angular acceleration coefficients may be decomposed to isolate $\vec{d}_{12}$ terms, where $\vec{d}_{12} = (d_x, d_y, d_z)$ $$\Delta a_{tangential_x} = \frac{\Delta\omega_y}{\Delta t}d_z - \frac{\Delta\omega_z}{\Delta t}d_y$$

$$\Delta a_{tangential_y} = \frac{\Delta\omega_z}{\Delta t}d_x - \frac{\Delta\omega_x}{\Delta t}d_z$$

$$\Delta a_{tangential_z} = \frac{\Delta\omega_x}{\Delta t}d_y - \frac{\Delta\omega_y}{\Delta t}d_x$$

The term $\vec{d}_{12_{proj}}$ can also be written as:

$$\vec{d}_{12_{proj}} = \vec{d}_{12} - (\vec{d}_{12} \cdot \vec{A})\vec{A} = \frac{1}{\omega^2}(\Delta\vec{a}_{tangential} - \Delta\vec{a}_{total})$$

Based on the definition of projection, $$(\vec{d}_{12} \cdot \vec{A})\vec{A} = \begin{bmatrix} d_x \\ d_y \\ d_z \end{bmatrix} \begin{bmatrix} A_x^2 & A_xA_y & A_xA_z \\ A_xA_y & A_y^2 & A_yA_z \\ A_xA_z & A_yA_z & A_z^2 \end{bmatrix}$$

where $\vec{d}_{12} = (d_x, d_y, d_z)$ is unknown and $\Delta\vec{a}_{total} = (\Delta a_x, \Delta a_y, \Delta a_z)$ is known.

$$(1 - A_x^2)d_x + (-A_xA_y)d_y + (-A_xA_z)d_z = \frac{1}{\omega^2}(\Delta a_{tangential_x} - \Delta a_x)$$

$$(-A_xA_y)d_x + (1 - A_y^2)d_y + (-A_yA_z)d_z = \frac{1}{\omega^2}(\Delta a_{tangential_y} - \Delta a_y)$$

$$(-A_xA_z)d_x + (-A_yA_z)d_y + (1 - A_z^2)d_z = \frac{1}{\omega^2}(\Delta a_{tangential_z} - \Delta a_z)$$

By regrouping the coefficients of the three unknowns ($d_x$, $d_y$, $d_z$), $$(A_x^2 - 1)\omega^2 d_x + \left(A_xA_y\omega^2 - \frac{\Delta\omega_z}{\Delta t}\right)d_y + \left(A_xA_z\omega^2 + \frac{\Delta\omega_y}{\Delta t}\right)d_z = \Delta a_x$$

$$\left(A_xA_y\omega^2 + \frac{\Delta\omega_z}{\Delta t}\right)d_x + (A_y^2 - 1)\omega^2 d_y + \left(A_yA_z\omega^2 - \frac{\Delta\omega_x}{\Delta t}\right)d_z = \Delta a_y$$

$$\left(A_xA_z\omega^2 - \frac{\Delta\omega_y}{\Delta t}\right)d_x + \left(A_yA_z\omega^2 + \frac{\Delta\omega_x}{\Delta t}\right)d_y + (A_y^2 - 1)\omega^2 d_z = \Delta a_z$$

Thus, for every instantaneous movement, three equations are obtained and three unknowns ($d_x$, $d_y$, $d_z$), namely the distance value of the distance vectors. This may be solved as a linear system of equations, by the distance calculating module 22 of the processor unit 20.

To reduce the impact of sensor errors, several instantaneous acquisitions, i.e., acquisitions at different time periods, may be obtained and compiled, averaged, analyzed to calculate the distance with one or more of the acquisitions. In an embodiment, the several instantaneous acquisitions are combined to a value of $\vec{d}_{12}$ which minimizes the overall error. This can be done by the distance calculating module 22 of the processor unit 20 by solving the following linear system with singular value decomposition (SVD).

$$\begin{bmatrix} (A_{x_1}^2 - 1)\omega_1^2 & \left(A_{x_1}A_{y_1}\omega_1^2 - \frac{\Delta\omega_{z_1}}{\Delta t_1}\right) & \left(A_{x_1}A_{z_1}\omega_1^2 + \frac{\Delta\omega_{y_1}}{\Delta t_1}\right) \\ \left(A_{x_1}A_{y_1}\omega_1^2 + \frac{\Delta\omega_{z_1}}{\Delta t_1}\right) & (A_{y_1}^2 - 1)\omega_1^2 & \left(A_{y_1}A_{z_1}\omega_1^2 - \frac{\Delta\omega_{x_1}}{\Delta t_1}\right) \\ \left(A_{x_1}A_{z_1}\omega_1^2 - \frac{\Delta\omega_{y_1}}{\Delta t_1}\right) & \left(A_{y_1}A_{z_1}\omega_1^2 + \frac{\Delta\omega_{x_1}}{\Delta t_1}\right) & (A_{z_1}^2 - 1)\omega_1^2 \\ & \cdots & \\ (A_{x_n}^2 - 1)\omega_n^2 & \left(A_{x_n}A_{y_n}\omega_n^2 - \frac{\Delta\omega_{z_n}}{\Delta t_n}\right) & \left(A_{x_n}A_{z_n}\omega_n^2 + \frac{\Delta\omega_{y_n}}{\Delta t_n}\right) \\ \left(A_{x_n}A_{y_n}\omega_n^2 + \frac{\Delta\omega_{z_n}}{\Delta t_n}\right) & (A_{y_n}^2 - 1)\omega_n^2 & \left(A_{y_n}A_{z_n}\omega_n^2 - \frac{\Delta\omega_{x_n}}{\Delta t_n}\right) \\ \left(A_{x_n}A_{z_n}\omega_n^2 - \frac{\Delta\omega_{y_n}}{\Delta t_n}\right) & \left(A_{y_n}A_{z_n}\omega_n^2 + \frac{\Delta\omega_{x_n}}{\Delta t_n}\right) & (A_{z_n}^2 - 1)\omega_n^2 \end{bmatrix}$$

$$\begin{bmatrix} d_x \\ d_y \\ d_z \end{bmatrix} = \begin{bmatrix} \Delta a_{x_1} \\ \Delta a_{y_1} \\ \Delta a_{z_1} \\ \ldots \\ \Delta a_{x_n} \\ \Delta a_{y_n} \\ \Delta a_{z_n} \end{bmatrix}$$

Hence, the distance value of the vector ($d_x$, $d_y$, $d_z$) between the fixed positions of the accelerometer units 30 on the bone is obtained. An anatomy locator module 23 may factor in additional geometrical data obtained from the database 24, such as the distance of the accelerometer units 30 from the bone. For example, the anatomy locator module 23 may take into account the geometry of the support bracket 31A and/or of the self-centering mechanism 31B, in determining the distance between the fixed points on the bone B. The support bracket 31A and the self-centering mechanism 31B offset the accelerometer units 30 from the bone. The anatomy locator module 23 may remove this offset when calculating the position on the bone.

There are conditions to respect in a practical setup in order for the distance calculation to be accurate. The sensors are fixed to a body, i.e., the bone B, and their positions relative to the bone B do not change during their data acquisition. Also, the relative orientation between the sensors must be known and must not change during the acquisition.

The interface 50 then outputs the distance between the first fixed position and the second fixed position on the bone B, among other information. The distance may be in the form of a confirmation that the distal cut is at the adequate planned distance, etc. For example, the system 10 may benefit from an operative planning data file that is specific to the patient, and featuring planning data, such as distal cut depth, tibial length, implant size, etc. The processor unit 20 may include or access this information. Accordingly, the processor unit 20 may verify, using the operative planning data, that the distal cut is at a predetermined distance from a midpoint of the malleoli, taking into consideration for example a thickness of bone resected from the tibial (e.g., as a function of a tibial plateau implant), and the method may calculate this distance. The tibial cut may thus be validated by comparing the calculated distance value with the planned distance value. While the system 10 is described above as outputting a distance between fixed positions on the bone, the system 10 may add some functionalities, for instance if the accelerometers units 30 and the gyroscope 40 add the feature of determining orientations as well. For example, if the relative position and relative orientation of the sensors is known, the varus/valgus and flexion/extension angles of the distal cut may be calculated in the embodiment of FIG. 2. The determination of the orientation may be as described in U.S. Pat. No. 9,115,998, incorporated herein by reference. As an alternative approach, if a gyroscope unit 40 is fixated to each reference unit 30, the relative orientation T between first and second gyroscopes can be numerically calculated by SVD by solving the following set of equations, for each accelerometer n, T×g1=g2, wherein T is the 3×3 transformation matrix indicating a relative orientation of reference units 1 and 2, g1_n is the angular rates of change (a.k.a., angular velocity) measured by the gyroscope unit 40 of the first reference unit 30 measured at time n, and g2_n is the angular rates of change measured by the gyroscope unit 40 of the second reference unit 2 measured at time n. The measurements from the gyroscope units 40 are compared to use a difference between the measurements to determine a relative orientation between the gyroscope units 40. Accordingly, by the simultaneous steps of obtaining acceleration data and angular rates of change (61 and 62 in FIG. 3 described below), the system 10 may obtain the data necessary to also determine the relative orientation between anatomical landmarks (e.g., distal cut plane, malleoli axis) associated with the first fixed position and the second fixed position. In such a case, 64 (in FIG. 3, described below) also includes calculating a relative orientation between the first fixed position and the second fixed position. In the example of tibial cut validation, the validation of the orientation of the tibial cut plane may be performed.

Figure 3:
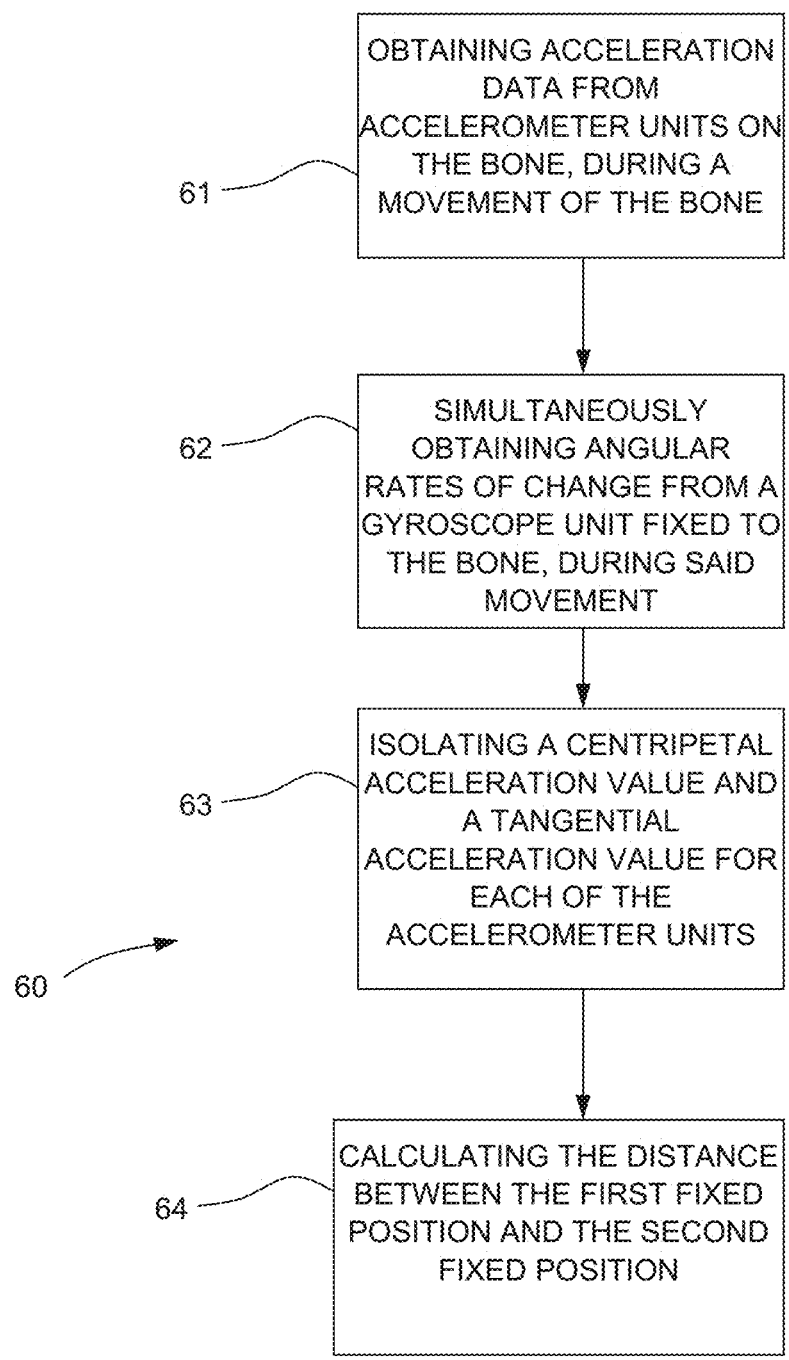
FIG. 3 is a flow chart of a method for calculating a distance between at least two points relative to a bone.

Referring to FIG. 3, a method for calculating a distance between at least two points on the bone B is generally shown at 60.

According to 61, at a moment t, first acceleration data is obtained from the first accelerometer unit 30A located at a first fixed location on the bone, during a movement of the bone. Second acceleration data is simultaneously obtaining from the second accelerometer unit 30B, at a second fixed location relative to the bone, during the movement. The acceleration data of other accelerometer units 30 may be obtained if applicable.

According to 62, angular rates of change are simultaneously obtained from the gyroscope unit(s) 40 fixed to the bone, during the movement. In 61 and 62, instant values are obtained. However, several instantaneous acquisitions may be combined, for example at different time periods.

According to 63, a centripetal acceleration value and a tangential acceleration value are isolated for the accelerometer units 30 by comparing the first acceleration data with the second acceleration data. Other approaches may be taken to compare the comparing the first acceleration data with the second acceleration data.

According to 64, the distance between the first fixed position and the second fixed position on the bone B is calculated using the angular rates of change of the gyroscope unit 40, and the centripetal acceleration value and the tangential acceleration value of the accelerometer units as in 63. The orientation between the first fixed position and the second fixed position may also be calculated using the readings of the numerous gyroscope units 40, if more than one is provided. Singular value decomposition may be used in the calculations if numerous instantaneous acquisitions have been combined. Other geometrical data may be used in the calculation, such as a geometry of a sensor support.

Among contemplated applications, in addition to the tibial cut validation as exemplified by FIG. 2, the system 10 and/or method 60 may be used to determine the length of various bones after resection, as well as orientation of cut planes. In an example, the system 10 and method 60 may be used in hip surgery. In this embodiment, one of the accelerometer units 30 may be mounted to the femur proximal to the femoral head, or to a femoral implant, in such a way that its distance relative to the center of rotation of the hip joint is known. For instance, the support bracket 31 may clamp onto the femoral implant in a known manner, before or after the assembly of the ball head. The geometrical relation between the accelerometer 30, the support bracket 31 and the femoral implant would be known and used in 64 to calculate the distance value to the center of rotation of the hip joint. A similar approach may be taken to measure the center of rotation of the shoulder joint, by having the support bracket 31 attaching to the humerus implant.

The invention claimed is:

1. A method for calculating a distance between at least two points on a bone, comprising:

obtaining, using one or more processors within a computing system, first acceleration data from a first accelerometer unit located at a first fixed location relative to the bone, during a movement of the bone;

simultaneously obtaining, using the one or more processors within the computing system, second acceleration data from at least a second accelerometer unit at a second fixed location relative to the bone, during said movement of the bone;

simultaneously obtaining, using the one or more processors within the computing system, angular rates of change from at least one gyroscope unit fixed to the bone, during said movement of the bone; and calculating and outputting, using the one or more processors within the computing system, a distance value of a distance vector between the first fixed location and the second fixed location using the angular rates of change of the at least one gyroscope unit and the first acceleration data and the second acceleration data of the accelerometer units.

2. The method according to claim 1, wherein calculating the distance value comprises isolating, using the one of more processors within the computing system, a centripetal acceleration value and a tangential acceleration value for the accelerometer units by comparing the first acceleration data and the second acceleration data, and calculating and outputting, using the one or more processors within the computing system, the distance value of the distance vector using the centripetal acceleration value and the tangential acceleration value of said first and second accelerometer units.

3. The method according to claim 1, further comprising obtaining third acceleration data of a third accelerometer unit at a third fixed location relative to the bone simultaneously with obtaining the first acceleration data, the second acceleration data and the angular rates of change, and wherein calculating and outputting the distance value comprises calculating and outputting the distance values of the distance vectors between the first fixed location, the second fixed location and the third fixed location.

4. The method according to claim 1, wherein simultaneously obtaining the first acceleration data, the second acceleration data and the angular rates of change includes simultaneously obtaining the first acceleration data, the second acceleration data and the angular rates of change at least at a first time period and a second time period, and wherein calculating the distance value comprises using data from the first time period and the second time period.

5. The method according to claim 4, wherein using data from the first time period and the second time period includes performing singular value decomposition with said data.

6. The method according to claim 1, wherein the first accelerometer unit is positioned at a tibial cut, and further comprising validating a depth of the tibial cut by comparing the distance value with a planned distance value.

7. The method according to claim 1, wherein the first accelerometer unit is positioned on a femur, and further comprising calculating leg length discrepancy by comparing the distance value with a pre-operative distance.

8. The method according to claim 1, wherein the first and second accelerometer units are positioned on a humerus, and further comprising calculating a humerus length.

9. The method according to claim 1, wherein at least one of first and second accelerometer units is offset from its fixed location relative to the bone by a support, and wherein calculating the distance value includes removing the offset from the geometry of the support.

10. The method according to claim 1, wherein the first and second accelerometer units are paired with a respective one of the at least one gyroscope unit, the method further comprising calculating and outputting, using the one or more processors within the computing system, a relative orientation between anatomical landmarks at the first fixed location and the second fixed location using the angular rates of change of the gyroscope units.

* * * * *